(12) United States Patent
Karacali et al.

(10) Patent No.: US 12,731,358 B2

(45) Date of Patent: Sep. 8, 2026

(54) ODOR SENSOR WITH ODOR IMAGE CONVERSION AND DEEP LEARNING

(71) Applicant: ATATÜRK ÜNIVERSITESI FIKRI MÜLKIYET HAKLARI KOORDINATÖRLÜĞÜ DÖNER SERMAYE ISLETMESI, Yakutiye (TR)

(72) Inventors: Tevhit Karacali, Yakutiye (TR); Mehmet Ertuğrul, Yakutiye (TR); Hasan Efeoğlu, Yakutiye (TR); Ibrahim Yücel Özbek, Yakutiye (TR); Elif Akarsu, Yakutiye (TR); Emin Argun Oral, Yakutiye (TR); Ömer Çoban, Yakutiye (TR); Ferda Dal, Yakutiye (TR); Yaşar Demir, Yakutiye (TR)

( * ) Notice: Subject to any disclaimer, the term of this patent is extended or adjusted under 35 U.S.C. 154(b) by 225 days.

(21) Appl. No.: 18/838,110

(22) PCT Filed: Dec. 19, 2023

(86) PCT No.: PCT/TR2023/051591

§ 371 (c)(1),
(2) Date: Aug. 13, 2024

(87) PCT Pub. No.: WO2024/136817

PCT Pub. Date: Jun. 27, 2024

(65) Prior Publication Data

US 2025/0037407 A1 Jan. 30, 2025

(30) Foreign Application Priority Data

Dec. 20, 2022 (TR) ................................ 2022/019745

(51) Int. Cl.

*G06V 10/14* (2022.01)
*G01N 33/00* (2006.01)

(Continued)

(52) U.S. Cl.

CPC ......... *G06V 10/14* (2022.01); *G01N 33/0027* (2013.01); *G06V 10/60* (2022.01); *G06V 10/77* (2022.01); *G06V 20/40* (2022.01)

(58) Field of Classification Search

CPC ......... G06V 10/14; G06V 10/60; G06V 10/77; G06V 20/40; G01N 33/0027; G01N 21/77; G01N 21/41; G01N 2021/7776

See application file for complete search history.

(56) References Cited

U.S. PATENT DOCUMENTS

2015/0048178 A1 2/2015 Edwards et al.
2022/0146415 A1* 5/2022 Putkaradze ........ G01N 33/0001

FOREIGN PATENT DOCUMENTS

AU 2021100368 A4 4/2021
CN 111443165 B 6/2021

(Continued)

OTHER PUBLICATIONS

International Search Report for corresponding PCT/TR2023/051591, dated Feb. 28, 2024.

(Continued)

*Primary Examiner* — Mekonen T Bekele

(74) *Attorney, Agent, or Firm* — Egbert, McDaniel & Swartz, PLLC

(57) ABSTRACT

A system with odor image conversion and deep learning and a two-stage integrated structure that identifies and determines the concentration of volatile chemical vapors and/or evaporated chemicals by changing the optical filter behavior of the optical chemical sensor produced in the first stage when it is affected by chemical vapors and by changing the beam spectrum passing through this filter, and by processing the sensor data with deep learning algorithms using image processing techniques in the second stage.

5 Claims, 1 Drawing Sheet

(51) Int. Cl.

| | |
|---|---|
| ***G06V 10/60*** | (2022.01) |
| ***G06V 10/77*** | (2022.01) |
| ***G06V 20/40*** | (2022.01) |

(56) References Cited

FOREIGN PATENT DOCUMENTS

| | | | |
|---|---|---|---|
| EP | 3187852 | A1 | 7/2017 |
| KR | 20220135469 | A | 10/2022 |

OTHER PUBLICATIONS

Written Opinion of the International Searching Authority for corresponding PCT/TR2023/051591, dated Feb. 28, 2024.

* cited by examiner

ODOR SENSOR WITH ODOR IMAGE CONVERSION AND DEEP LEARNING

FIELD OF THE INVENTION

This invention relates to a system with a two-stage integrated structure that identifies and determines the concentration of volatile chemical vapors and/or evaporated chemicals by changing the optical filter behavior of the optical chemical sensor produced in the first stage when it is affected by chemical vapors and by changing the beam spectrum passing through this filter, by processing the sensor data with deep learning algorithms using image processing techniques in the second stage.

STATE OF THE ART

Odor is any of a number of chemicals, usually dissolved in the air in very low concentrations, that are sensed through the nose. It is the differences between molecules that give odors their characteristic quality. In addition to comfort areas such as aroma and perfume, chemical molecules can be detected with odor sensors in areas that directly affect life such as industry, health and food.

Organic solvents are widely used in large quantities in the chemical industry and laboratories. Most organic solvents are organic chemicals with dangerous and toxic properties. Therefore, even at very low concentrations, they cause environmental pollution and harm to human health. Methanol, for example, can cause blindness and even threaten human life at concentrations of only a few percent in alcoholic beverages, while prolonged exposure to excessive levels of benzene in the air can cause leukemia and a potentially fatal blood cancer.

It is therefore important to find a method to determine the concentration of organic solvents with high sensitivity and low cost in industry, medicine, food safety and environmental control. In addition, many harmful gases are either odorless or very difficult to detect.

Detecting harmful gases and organic solvents has become even more important with advancing technology in industry, healthcare and military applications. So far, studies have generally tried to measure the type and concentration of the gas or odor by examining the change in physical parameters such as the conductivity of the sensor active substance as a result of its interaction with the gas. Problems such as response time, selectivity and sensitivity of these sensors are still awaiting solutions.

The major disadvantage of existing chemical sensors is that identification and concentration of the chemical cannot be done simultaneously.

In the patent document numbered KR2022135469A, which is in the known state of the art regarding the subject, the system is designed for hospitals with a unit that recognizes gases with a sensor and a unit that identifies with deep learning and classifies using neural networks, there is no image conversion algorithm.

Another patent document numbered CN111443165B in the art, states that deep learning-based industrial production, medical, environmental and security identification by converting odor into graphics.

In document numbered TH18049U in the art, which is also available in the art, identification is made by converting the perception of the odor sensor into signals.

In the patent document numbered AU2021100368A4, which is in the known state of the art, the classification results are displayed on an imaging device by means of a convolutional neural network after collecting the gas to be detected that interacts with the sensor and obtaining raw odor data from it.

When the studies in the state of the art are examined, due to the limitations of existing gas sensor technologies, both the development of sensor active materials and the limitations of the existing sensor mechanisms used, the development of next generation sensors has become important and it is understood that innovations in this field will be needed even more in the near future.

BRIEF DESCRIPTION OF THE INVENTION

This invention relates to a system, which fulfills the above-mentioned requirements, eliminates all disadvantages and brings some additional advantages, identifies and determines the concentration of volatile chemical vapors and/or evaporated chemicals by changing the optical filter behavior of the optical chemical sensor produced in the first stage with a two-stage integrated structure when it is affected by chemical vapors and by changing the beam spectrum passing through this filter, by processing the sensor data with deep learning algorithms using image processing techniques in the second stage.

The primary object of the present invention is the change in the optical filter behavior of the optical chemical sensor when it is affected by chemical vapors, and the change in the spectrum of the light passing through this filter, and the change in the pattern caused by the change in intensity in the sensor image falling on the camera.

Another object of the present invention is to process the sensor data, where deep learning algorithms using image processing techniques are more effective in machine learning.

A further object of the present invention is the identification and concentration determination of volatile chemical vapors or vaporized chemicals with very high sensitivity.

The structural and characteristic features of the present invention will be understood clearly by the following detailed description. Therefore the evaluation shall be made by taking this detailed description into consideration.

DETAILED DESCRIPTION OF THE INVENTION

In this detailed description, odor sensor with odor image conversion and deep learning is described only for clarifying the subject matter in a manner such that no limiting effect is created.

This invention relates to a system with a two-stage integrated structure that identifies and determines the concentration of volatile chemical vapors and/or evaporated chemicals by changing the optical filter behavior of the optical chemical sensor produced in the first stage when it is affected by chemical vapors and by changing the beam spectrum passing through this filter, by processing the sensor data with deep learning algorithms using image processing techniques in the second stage.

The invention in its most preferred form is the odor sensor with odor to image conversion and deep learning.

Figure 1:
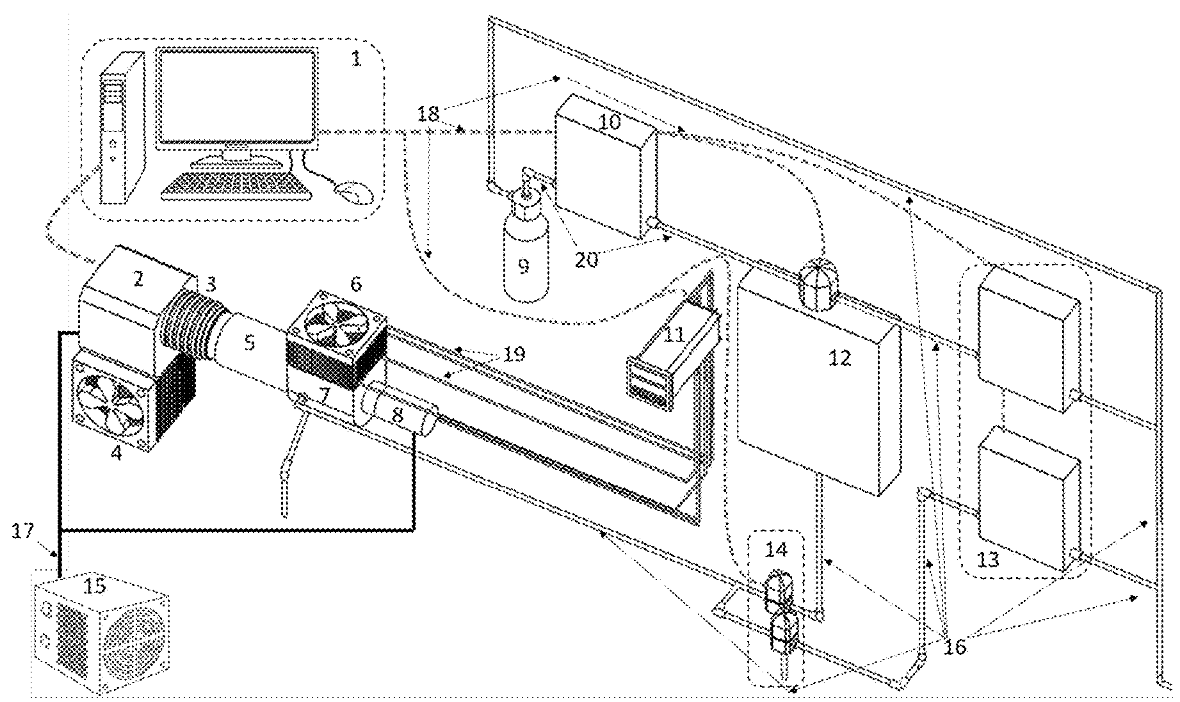
FIG. 1 illustrates the system of the present invention.

FIG. 1 shows a system for image conversion of odor from a porous silicon sensor with a porous silicon sensor active region, integrated with a light source and a camera.

The system given in FIG. 1 consists of the following;

i. Test cell enclosing the optic pathway (3, 5, 6, 7, 8), ii. The part where the chemical vapor is produced and diluted (9, 10, 12, 13, 14), iii. Temperature control (11, 20), iv. Image receiving camera (2, 4), v. Computer for instrument control and data acquisition (1)

vi. 2 solenoid valve (14)

components

The numbered parts of the system given in FIG. 1 are as follows in detail:

1. Controller computer (PC) used to control all devices.
2. Camera used to take images from the sensor (visible region, infrared, short wavelength infrared, etc.).
3. Camera lens and cooling block.
4. Camera cooler (aluminum block with fan).
5. Optical path (Connects the sensor cell and the camera. It prevents ambient light from entering and ensures that the sensor image is clearly formed in the camera).
6. Sensor cell cooler (Peltier cooler, Fan, Aluminum block).
7. Sensor measuring cell (Teflon inside, aluminum outside, controlled steam inlet and outlet, chamber with heating lamp and thermocouple).
8. Light source (sources emitting light in the visible or infrared region, illuminators, laser and LED sources).
9. The chamber containing the chemical (glass or borosilica glass, the chemical to be measured is pushed into the liquid flow controller by the pressure of the gas sent into this chamber).
10. Liquid flow control unit (The chemical to be sent to the test cell is controlled by this unit).
11. Temperature control unit (Step controller, this unit is used to keep the internal temperature of the cell where the sensor measurement is to be performed constant at the desired temperature).
12. The vapor extraction system of the chemical (the vapor to be sent to the measuring cell is vaporized and diluted here).
13. Gas flow control units (Diluent and sweeper gases are controlled by these units).
14. Solenoid valves (The prepared chemical is directed into the test cell through these valves).
15. Power supply (Provides energy for light source, camera, temperature controller, liquid flow controller, gas flow controllers, vaporizer, solenoid valves).
16. Gas carrier pipes (6 mm stainless steel pipe).
17. Power supply cables (for camera and light source).
18. Cables for communication between control devices and PC.
19. Cables for communication between the Peltier cooler, lamp and thermocouple and the temperature controller.
20. Liquid carrier pipes (6 mm stainless steel pipe).

Figure 2:
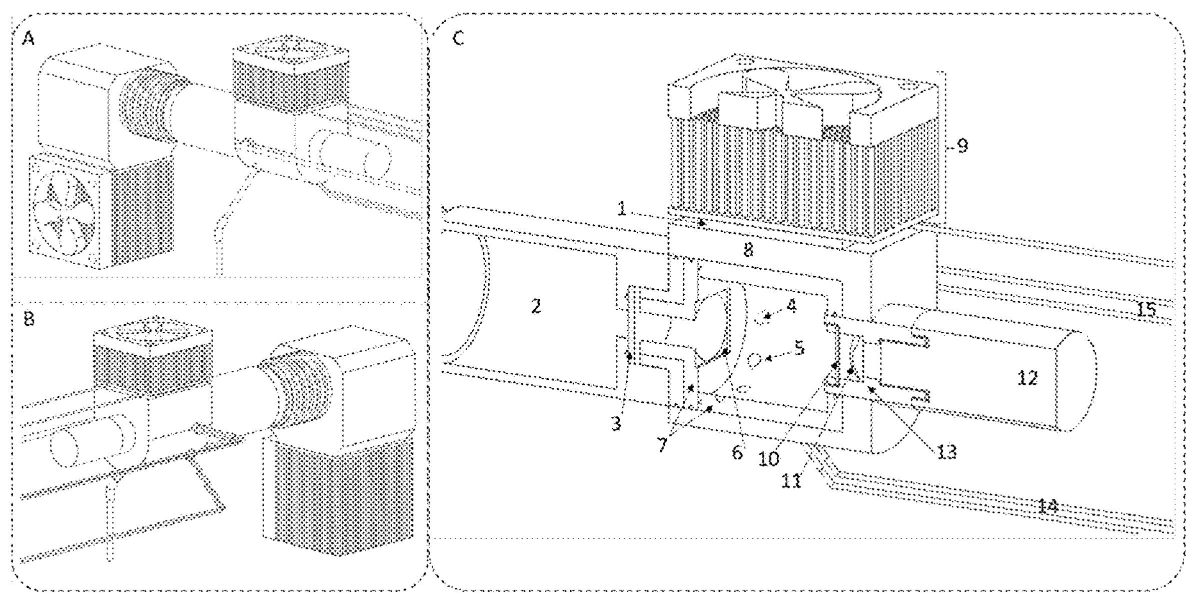
FIG. 2 is a detailed view of the measurement system thereof.

FIG. 2 shows a detail view of the measurement system, consisting of the camera, light source and test cell. FIG. 2 shows (A) the right view of the part consisting of camera, light source and test cell, (B) the left view of the part consisting of camera, light source and test cell, (C) the interior of the test cell part.

The measurement system given in FIG. 2 (C) is as follows in detail:

1. Peltier cooler (used for cooling the test cell).
2. Optical path (Used to reduce the sensor image to the camera at the desired scale. It also prevents outside light from entering the camera. Made of aluminum).
3. Glass or borosilicate glass (used to prevent chemical vapor from passing from the test cell to the camera).
4. Heating lamp (used to bring the sensor surface to the desired temperature and remove the chemical vapor from the sensor).
5. Thermocouple (used for monitoring and controlling the temperature of the test cell).
6. The location where the porous silicon is placed (the fabricated porous silicon is placed here).
7. Teflon layer (the layer that forms the inner surface of the test cell).
8. Aluminum layer (layer forming the outer surface of the test cell).
9. Aluminum heat sink with fan (used to remove the heat generated in the Peltier).
10. Glass or borosilicate glass (used to prevent chemical vapor from passing from the test cell to the light source).
11. Optical lens (used to focus the light of the light source onto porous silicon).
12. Light source (used to illuminate the porous silicon surface).
13. Connection apparatus (connects the light source and the test cell).
14. Thermocouple cables.
15. Heating lamp cables.

The rays passing through the 1 cm×1 cm porous silicon illuminated by the light source from above form an image on the camera below, while the rays coming from the light source and reaching the camera form a pattern of a very large number of pixels on the camera due to the porous silicon. When exposed to odor, the effective refractive index changes as the pores are partially or completely filled with odor and/or gas, thus changing the image that falls into the camera. The image formed in the camera varies depending on the type of odor and/or gas, its concentration and even the direction of arrival into the porous silicon. Using the video images obtained from the camera, deep learning algorithms detect the type and concentration of the odor and/or gas in a very short time and with very high sensitivity, since the image obtained from millions of pixels is used simultaneously.

As an operating method, the porous silicon sensor is placed in the test cell at location 6 in FIG. 2 (C), the light from the light source is incident on the sensor surface and the light passing through the sensor reaches the camera to obtain an image. After the temperature on the sensor surface of the test cell is heated to the desired temperature with the elements numbered 11 shown in FIG. 1 and numbered 4 and 5 shown in FIG. 2 (C), while the temperature of the test cell is reduced to room temperature with the elements numbered 11 given in FIG. 1 and numbered 1 and 9 given in FIG. 2 (C), Nitrogen gas is sent to the test cell at constant flow with the gas flow control units numbered 13 given in FIG. 1 and the camera recording is started after the temperature is stabilized. After the sensor is exposed to nitrogen gas for the first 120 seconds of the camera recording, the chemical vapor obtained with the components shown in FIG. 1 with numbers 9, 10, 12, 13 is sent to the test cell and the video of the sensor under chemical vapor is taken for 120 seconds. Then the vapor is cut off and nitrogen is flowed into the test cell and the video of the sensor under nitrogen is taken for 120 s and the video of the sensor image in the camera is collected under nitrogen environment and chemical vapor and the difference between the image formed in the camera under chemical vapor and the image formed under nitrogen gas due to the porous structure of the sensor is separated by image processing and artificial intelligence methods, and the odor and/or gas is identified and its concentration is determined.

By converting the odor with all these features into an image and using deep learning, the type and concentration of the odor and/or gas subject to the invention with the odor sensor will be detected in a very short time and sensitivity by converting it into an image and the existing problems specific to this process will be eliminated.

Detecting harmful gases and organic solvents in the field of the invention with the inventive sensor provides improvements in industry, health and military applications.

The invention claimed is:

1. A system that identifies and determines the concentration of volatile chemical vapors and/or evaporated chemicals by processing sensor data with deep learning algorithms using image processing techniques of the pattern change caused by the change in intensity change in the sensor image falling on the camera due to the change in the light spectrum passing through the porous silicon filter as a result of the change in the optical filter behavior when the odor sensor is affected by chemical vapors with a two-stage integrated structure with image conversion and deep learning, wherein the system comprises:

i. test cell enclosing the optic pathway,
ii. the part where the chemical vapor is produced and diluted,
iii. image receiving camera,
iv. computer for instrument control and data acquisition, and
v. 2 solenoid valve components.

2. A method according to claim 1, wherein the test cell of the measurement system comprises:

i. Peltier cooler,
ii. optical pathway,
iii. glass or borosilicate glass,
iv. heating lamp,
v. thermocouple,
vi. porous silicon sensor,
vii. teflon layer,
viii. aluminium layer,
ix. aluminum cooler with fan,
x. optical lens,
xi. light source,
xii. connection apparatus,
xiii. thermocouple cables, and
xiv. heating lamp cables.

3. A method according to claim 2, wherein it is an integrated system comprising of a test cell containing the optical path, the part where the chemical vapor is produced and diluted, an image acquisition camera, a computer for instrument control and data acquisition, and 2 solenoid valves.

4. A method according to claim 2, wherein it takes a video image from the sensor and determines the concentration amount together with chemical vapor identification with the help of the test cell, which includes a light source and a camera.

5. A method according to claim 2, wherein it provides a pattern change in the sensor image falling on the camera due to the change in intensity caused by the change in the spectrum of light passing through the porous silicon filter.

* * * * *